United States Patent
Tijerina et al.

(10) Patent No.: US 10,135,819 B2
(45) Date of Patent: Nov. 20, 2018

(54) WEARABLE DEVICE AUTHENTICATION

(71) Applicant: PAYPAL, INC., San Jose, CA (US)

(72) Inventors: Kevin Keith Tijerina, Pflugerville, TX (US); Abraham Doris-Down, Newtonville, MA (US); Matthew Alexander Wilczynski, Austin, TX (US); Miguel Angel Escobedo, Austin, TX (US)

(73) Assignee: PAYPAL, INC., San Jose, CA (US)

( * ) Notice: Subject to any disclaimer, the term of this patent is extended or adjusted under 35 U.S.C. 154(b) by 0 days.

(21) Appl. No.: 15/389,893

(22) Filed: Dec. 23, 2016

(65) Prior Publication Data
US 2017/0111356 A1  Apr. 20, 2017

Related U.S. Application Data (63) Continuation of application No. 14/582,876, filed on Dec. 24, 2014, now abandoned, and a continuation of
(Continued)

(51) Int. Cl.
*G06F 7/04* (2006.01)
*H04L 29/06* (2006.01)
(Continued)

(52) U.S. Cl.
CPC .......... *H04L 63/0861* (2013.01); *A61B 5/01* (2013.01); *A61B 5/021* (2013.01); *A61B 5/024* (2013.01); *A61B 5/02055* (2013.01); *A61B 5/0402* (2013.01); *A61B 5/117* (2013.01); *A61B 5/14532* (2013.01); *A61B 5/14551* (2013.01); *A61B 5/681* (2013.01); *A61B 5/6803* (2013.01); *A61B 5/7246* (2013.01); *G06F 21/32* (2013.01);
(Continued)

(58) Field of Classification Search
CPC . H04L 63/0861; H04L 67/306; A61B 5/7246; A61B 5/681; A61B 5/02055; A61B 5/117; A61B 5/6803
USPC .......................................................... 726/7
See application file for complete search history.

(56) References Cited

U.S. PATENT DOCUMENTS 7,477,890 B1   1/2009  Narayanaswami
2002/0190125 A1  12/2002  Stockhammer
(Continued)

OTHER PUBLICATIONS

Costaguta, Elizabeth, "Getting to the Heart of Password Protection", nymi, Dec. 3, 2013, 12 pages, https://lizcostaguta.files.wordpress.com/2014/01/nymi_whitepaper.pdf, Retrieved date: Jan. 23, 2016.
(Continued)

*Primary Examiner* — Mohammad W Reza
(74) *Attorney, Agent, or Firm* — Haynes and Boone, LLP (57) ABSTRACT

A wearable device is used to authenticate a user into a user account at a user device of the user. In particular, the wearable device may include a sensor configured to detect a body chemistry of the user. The wearable device may send a signal, such as a short range wireless signal, Bluetooth Low Energy or the like, to the user device to communicate the detected body chemistry to the user device. The user device may authenticate the user based on the body chemistry condition detected at the wearable device. In an embodiment, the wearable device may include an olfactory sensor configured to detect certain smell or scent of the user.

20 Claims, 7 Drawing Sheets

Related U.S. Application Data application No. PCT/US2015/063477, filed on Dec. 2, 2015.

(51) Int. Cl.

| | | |
|---|---|---|
| *H04W 4/80* | (2018.01) | |
| *A61B 5/0205* | (2006.01) | |
| *A61B 5/117* | (2016.01) | |
| *A61B 5/00* | (2006.01) | |
| *H04L 29/08* | (2006.01) | |
| *A61B 5/01* | (2006.01) | |
| *A61B 5/021* | (2006.01) | |
| *A61B 5/024* | (2006.01) | |
| *A61B 5/0402* | (2006.01) | |
| *A61B 5/145* | (2006.01) | |
| *A61B 5/1455* | (2006.01) | |
| *G06F 21/32* | (2013.01) | |
| *G06F 21/35* | (2013.01) | |
| *H04W 12/06* | (2009.01) | |
| *A61B 5/053* | (2006.01) | |

(52) U.S. Cl.
CPC .......... *G06F 21/35* (2013.01); *H04L 63/0853* (2013.01); *H04L 67/306* (2013.01); *H04W 4/80* (2018.02); *H04W 12/06* (2013.01); *A61B 5/0533* (2013.01)

(56) References Cited

U.S. PATENT DOCUMENTS

| | | | |
|---|---|---|---|
| 2006/0115130 A1 | 6/2006 | Kozlay | |
| 2006/0177061 A1 | 8/2006 | Orsini et al. | |
| 2007/0197261 A1 | 8/2007 | Humbel | |
| 2008/0062338 A1 | 3/2008 | Herzog et al. | |
| 2008/0216171 A1* | 9/2008 | Sano | H04L 9/32 726/19 |
| 2009/0094681 A1 | 4/2009 | Sadler et al. | |
| 2009/0270743 A1 | 10/2009 | Dugan et al. | |
| 2010/0274678 A1 | 10/2010 | Rolf et al. | |
| 2011/0016534 A1 | 1/2011 | Jakobsson et al. | |
| 2011/0102137 A1 | 5/2011 | Schröter | |
| 2011/0105022 A1 | 5/2011 | Vawter | |
| 2012/0050046 A1 | 3/2012 | Satorius | |
| 2012/0262275 A1 | 10/2012 | Schultz | |
| 2012/0316459 A1 | 12/2012 | Abreu | |
| 2013/0146659 A1 | 6/2013 | Zhou et al. | |
| 2013/0173461 A1 | 7/2013 | Levy | |
| 2013/0227651 A1 | 8/2013 | Schultz et al. | |
| 2013/0246260 A1 | 9/2013 | Barten et al. | |
| 2014/0085050 A1* | 3/2014 | Luna | G07C 9/00087 340/5.82 |
| 2014/0143149 A1 | 5/2014 | Aissi | |
| 2014/0157401 A1 | 6/2014 | Alameh et al. | |
| 2014/0247151 A1 | 9/2014 | Proud et al. | |
| 2014/0250515 A1 | 9/2014 | Jakobsson | |
| 2014/0279528 A1 | 9/2014 | Slaby et al. | |
| 2014/0283016 A1 | 9/2014 | Sambamurthy et al. | |
| 2014/0366111 A1 | 12/2014 | Sheller et al. | |
| 2015/0135310 A1* | 5/2015 | Lee | A61B 5/681 726/20 |
| 2015/0261946 A1* | 9/2015 | Yoon | G06F 21/34 726/19 |
| 2015/0317855 A1* | 11/2015 | Sezan | A61B 5/1171 340/5.52 |

OTHER PUBLICATIONS

Tamannagari, Gauthami, "Power Efficient Design of Finger-Ring Sensor for Patient Monitoring", University of Texas at San Antonio, Dec. 2008, p. 14, Figures 4.1b &4.2, https://books.google.com/books?id=FaL0b0sCRwMC&pg=PR4&dq=TAMANNAGARI,+GAUTHAMI,+%E2%80%9CPOWER+EFFICIENT+DESIGN+OF+FINGER-RING+SENSOR+FOR+PATIENT+MONITORING&hl=en&sa=X&ved=0ahUKEwjG2PKUhN_MAhVE62MKHfAIAj8Q6AEIKjAB#v=onepage&q=TAMANNAGARI%2C%20GAUTHAMI%2C%20%E2%80%9CPOWER%20EFFICIENT%20DESIGN%20OF%20FINGER-RING%20SENSOR%20FOR%20PATIENT%20MONITORING&f=false, Retrieved date: Jan. 23, 2016.

\* cited by examiner

FIG. 6

WEARABLE DEVICE AUTHENTICATION

CROSS REFERENCED TO RELATED APPLICATIONS

This continuation patent application claims priority to and the benefit of U.S. patent application Ser. No. 14/582,876, filed Dec. 24, 2014, and International Patent Application No. PCT/US2015/063477, filed Dec. 2, 2015, both of which are incorporated by reference in their entirety.

BACKGROUND

Field of the Invention

The present invention generally relates to wearable devices, and more particularly, to systems and methods for implementing authentication at the wearable devices.

Related Art

With the popularity of internet and online commerce, consumers increasingly are using online services for various transactions and interactions. For example, consumers may shop online, make electronic payments, and/or communicate electronically via email services or instant message services. Many of the online services require consumers to set up an account and login credentials. Consumers are then required to log in, such as entering a login ID and password, to be authenticated before consumers may use the services. Thus, the authentication process may be inconvenient for a consumer, especially when the consumer has a plurality of different service accounts that require different authentication credentials. Consequently, there is a need for an easier way to authenticate a consumer that is both secure and convenient.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

According to an embodiment, a wearable device is used to authenticate a user into a user account at a user device of the user. In particular, the wearable device may include a sensor configured to detect body chemistry conditions of the user. The system may authenticate the user based on the body chemistry conditions detected at the wearable device.

The system may compare the body chemistry conditions detected at the wearable device with the body chemistry profile of the user. The system may determine a similarity score indicating how closely the body chemistry conditions detected at the wearable device match those of the body chemistry profile of the user. The system may authenticate the user based on the similarity score.

In an embodiment, the wearable device may include an olfactory sensor configured to detect certain smells or scents of the user. For example, a smell or scent may be a natural smell or scent emitted from the user's body. In another example, a smell or scent may be a perfume or cologne worn by the user. When the olfactory sensor detects smells or scents that match those of the user's smells or scents, the wearable device may authenticate the user or send signals for authenticating the user to the user device. Based on the detected scent or smell at the wearable device, the wearable device or the user device may authenticate the user.

In an embodiment, the sensor may be a skin conductance sensor configured to detect a conductance of the user's skin. The sensor may be provided at an inner surface of the wearable device facing the user to contact the skin of the user when the wearable device is worn by the user. When the wearable device is worn by the user, the skin conductance sensor may detect and monitor the skin conductance of the user and the wearable device may determine whether the detected skin conductance matches that of the body chemistry profile of the user and whether the wearable device is still worn by the user. When the detected skin conductance no longer matches that of the user or the wearable device is taken off from the user, the wearable device may indicate to the user device that the wearable device is no longer worn by the user.

In an embodiment, the sensor of the wearable device may be a heart rate sensor configured to measure a heart rate and/or patterns of heart beats of the user. The heart rate sensor may detect and monitor the user's heart rate and/or patterns of the user's heart beat and may determine whether the wearable device is still worn by the user and whether the detected heart beat or heart rates match that of the user's heart beat or heart rate.

In an embodiment, the sensor may be a blood chemistry sensor, such as a blood glucose sensor (optical type) or blood chemistry sensor that detects histamine response of the user. In some embodiments, the sensor may be a blood oxygen level sensor or a blood pressure sensor. As such, the blood chemistry sensor may detect whether the wearable device is still worn by the user and whether the detected blood chemistry matches the blood chemistry defined in the user's body chemistry profile.

In an embodiment, the sensor may be a temperature sensor configured to detect a temperature. For example, the temperature sensor may detect a body temperature of the user and the ambient temperature of the user when the wearable device is worn by the user. The wearable device may detect how the user's body temperature responds to respective ambient temperature.

In an embodiment, a plurality of different sensors may be implemented together to detect various types of body chemistry of the user. A combination of different types of body chemistry may be used to provide risk/security assessment and/or user authentication. In an embodiment, a user may set up the wearable device to be used for user authentication with the user device. The user may designate or associate the wearable device for user authentication with certain accounts of the user. In an embodiment, one wearable device may be used for user authentication of multiple different user accounts. In another embodiment, multiple wearable devices may be used in combination for user authentication of a particular user account. As such, various combinations of wearable devices may be used for user authentication of different user accounts.

In an embodiment, the user device may automatically authenticate the user for a user account without requiring the user to enter credentials, such as passwords or login IDs, when the user device receives the signals from the wearable device indicating that the wearable device is worn by the user. In another embodiment, the user device may require a login credential for the initial login and may keep the user logged in as long as the user device receives the signals from the wearable device indicating that the wearable device is still worn by the user. The user device may log the user out of the account when the user device receives signals from the wearable device indicating that the wearable device is no longer worn by the user or is separated from the user. In an embodiment, if the user is logged out and the user device receives the unique signal from the wearable device, the user device may still require the user to provide credentials for logging in. The user device may keep the user logged in thereafter as long as the user device continues to receive the unique wireless signals from the wearable device.

In an embodiment, the wearable device may be a watch type device configured to provide time related information and be worn by the user. In another embodiment, the wearable device may be a jewelry type item, such as a ring, a necklace, a wrist band, and the like. In still another embodiment, the wearable device may be a belt, a neck tie, a tie pin, a collar stay, and any other wearable accessories. In still another embodiment, the wearable may be a clip or a tab configured to be attached to the user or other items carried by the user.

Using one or a combination of detected body chemistry or body data related to the user, the user can thus make a payment more easily without proactively entering an authenticator. In other embodiments, the various body data can be weighted differently, such that one type (more uniquely associated with the user) is weighted more than another type (such as perfume, soap, or cologne smell that can be associated with many different users).

Figure 1:
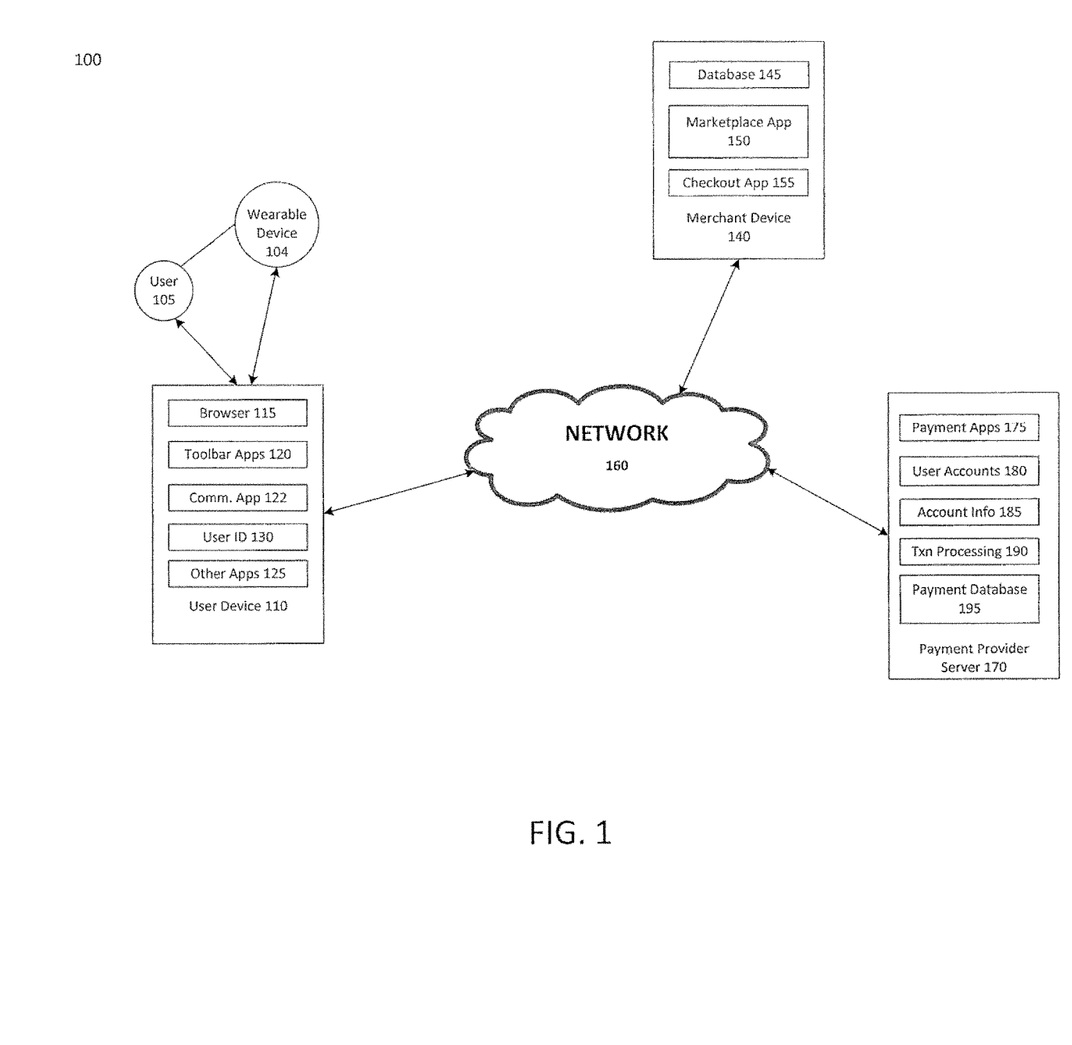
FIG. 1 is a block diagram of a networked system suitable for implementing wearable devices for user authentication according to an embodiment.

FIG. 1 is a block diagram of a networked system suitable for implementing wearable devices for user authentication according to an embodiment. Networked system 100 may comprise or implement a plurality of servers and/or software components that operate to perform various payment transactions or processes. Exemplary servers may include, for example, stand-alone and enterprise-class servers operating a server OS such as a MICROSOFT® OS, a UNIX® OS, a LINUX® OS, or other suitable server-based OS. It can be appreciated that the servers illustrated in FIG. 1 may be deployed in other ways and that the operations performed and/or the services provided by such servers may be combined or separated for a given implementation and may be performed by a greater number or fewer number of servers. One or more servers may be operated and/or maintained by the same or different entities.

System 100 may include a user device 110, a merchant server 140, and a payment provider server 170 in communication over a network 160. A wearable device 104 may be worn by user 105 and may communicate with user device 110. Payment provider server 170 may be maintained by a payment service provider, such as PayPal, Inc. of San Jose, Calif. A user 105, such as a sender or consumer, utilizes user device 110 to perform a transaction using payment provider server 170. User 105 may utilize user device 110 to initiate a payment transaction, receive a transaction approval request, or reply to the request. Note that transaction, as used herein, refers to any suitable action performed using the user device, including payments, transfer of information, display of information, etc. For example, user 105 may utilize user device 110 to initiate a deposit into a savings account. Although only one merchant server is shown, a plurality of merchant servers may be utilized if the user is purchasing products or services from multiple merchants.

In some embodiments, the user 105 may have a payment account at the payment provider server 170. The payment account may allow user 105 to purchase and/or pay for various products or services at a merchant. The user 105 may be required to enter credentials for user authentication at the user device 110 to access and use the payment account. The wearable device 104 may be associated with the payment account of the user 105 and be used for user authentication. The wearable device 104 may emit a wireless signal, such as Bluetooth signal, Bluetooth Low Energy (BLE) signal, or other Near-Field Communication (NFC) signals, to communicate body chemistry detected at the wearable device 104 or to indicate that the wearable device 104 is worn by the user 105. The user device may authenticate the user 105 based on the signal emitted from the wearable device 104.

User device 110, merchant server 140, payment provider server 170, and wearable device 104 may each include one or more processors, memories, and other appropriate components for executing instructions such as program code and/or data stored on one or more computer readable mediums to implement the various applications, data, and steps described herein. For example, such instructions may be stored in one or more computer readable media such as memories or data storage devices internal and/or external to various components of system 100, and/or accessible over network 160. Network 160 may be implemented as a single network or a combination of multiple networks. For example, in various embodiments, network 160 may include the Internet or one or more intranets, landline networks, wireless networks, and/or other appropriate types of networks.

User device 110 may be implemented using any appropriate hardware and software configured for wired and/or wireless communication over network 160. For example, in one embodiment, user device 110 may be implemented as a personal computer (PC), a smart phone, laptop computer, a wearable computing device, and/or other types of computing devices capable of transmitting and/or receiving data, such as an iPad™ from Apple™.

User device 110 may include one or more browser applications 115 which may be used, for example, to provide a convenient interface to permit user 105 to browse infoitiiation available over network 160. For example, in one embodiment, browser application 115 may be implemented as a web browser configured to view information available over the Internet, such as a user account for setting up a shopping list and/or merchant sites for viewing and purchasing products and services. User device 110 may also include one or more toolbar applications 120 which may be used, for example, to provide client-side processing for performing desired tasks in response to operations selected by user 105. In one embodiment, toolbar application 120 may display a user interface in connection with browser application 115.

User device 110 may further include other applications 125 as may be desired in particular embodiments to provide desired features to user device 110. For example, other applications 125 may include security applications for implementing client-side security features, programmatic client applications for interfacing with appropriate application programming interfaces (APIs) over network 160, or other types of applications.

Applications 125 may also include email, texting, voice and IM applications that allow user 105 to send and receive emails, calls, and texts through network 160, as well as applications that enable the user to communicate, transfer information, make payments, and otherwise utilize a smart wallet through the payment provider as discussed above. User device 110 includes one or more user identifiers 130 which may be implemented, for example, as operating system registry entries, cookies associated with browser application 115, identifiers associated with hardware of user device 110, or other appropriate identifiers, such as used for payment/user/device authentication. In one embodiment, user identifier 130 may be used by a payment service provider to associate user 105 with a particular account maintained by the payment provider. A communications application 122, with associated interfaces, enables user device 110 to communicate within system 100.

User device 110 may include a short distance communication device, such as a Bluetooth device or a Near-Field Communication (NFC) device configured to communicate with other devices located near the user device 110. The Bluetooth device may implement low energy Bluetooth (BLE) communication. For example, user device 110 may communicate with wearable device 104 via BLE or NFC communication to receive information regarding body chemistry detected at the wearable device 104.

Merchant server 140 may be maintained, for example, by a merchant or seller offering various products and/or services. The merchant may have a physical point-of-sale (POS) store front. The merchant may be a participating merchant who has a merchant account with the payment service provider. Merchant server 140 may be used for POS or online purchases and transactions. Generally, merchant server 140 may be maintained by anyone or any entity that receives money, which includes service providers as well as banks and retailers. Merchant server 140 may include a database 145 identifying available products (including digital goods) and/or services (e.g., collectively referred to as items) which may be made available for viewing and purchase by user 105. Accordingly, merchant server 140 also may include a marketplace application 150 which may be configured to serve information over network 160 to browser 115 of user device 110. In one embodiment, user 105 may interact with marketplace application 150 through browser applications over network 160 in order to view various products, food items, or services identified in database 145.

Merchant server 140 also may include a checkout application 155 which may be configured to facilitate the purchase by user 105 of goods or services online or at a physical POS or store front. Checkout application 155 may be configured to accept payment information from or on behalf of user 105 through payment service provider server 170 over network 160. For example, checkout application 155 may receive and process a payment confirmation from payment service provider server 170, as well as transmit transaction information to the payment provider and receive information from the payment provider (e.g., a transaction ID). Checkout application 155 may be configured to receive payment via a plurality of payment methods including cash, credit cards, debit cards, checks, money orders, or the like.

Payment provider server 170 may be maintained, for example, by an online payment service provider which may provide payment between user 105 and the operator of merchant server 140. In this regard, payment provider server 170 includes one or more payment applications 175 which may be configured to interact with user device 110 and/or merchant server 140 over network 160 to facilitate the purchase of goods or services, communicate/display information, and send payments by user 105 of user device 110.

Payment provider server 170 also maintains a plurality of user accounts 180, each of which may include account information 185 associated with consumers, merchants, and funding sources, such as banks or credit card companies. For example, account information 185 may include private financial information of users of devices such as account numbers, passwords, device identifiers, user names, phone numbers, credit card information, bank information, or other financial information which may be used to facilitate online transactions by user 105. In an embodiment, the account information 185 also may include information about wearable devices of the user 105 that are associated with the user account of the user 105 and that may be used to provide user authentication for accessing the user account. The account information 185 also may include body chemistry profile of the user 105. Advantageously, payment application 175 may be configured to interact with merchant server 140 on behalf of user 105 during a transaction with checkout application 155 to track and manage purchases made by users and which and when funding sources are used.

A transaction processing application 190, which may be part of payment application 175 or separate, may be configured to receive information from user device 110 and/or merchant server 140 for processing and storage in a payment database 195. Transaction processing application 190 may include one or more applications to process information from user 105 for processing an order and payment using various selected funding instruments, including for initial purchase and payment after purchase as described herein. As such, transaction processing application 190 may store details of an order from individual users, including funding source used, credit options available, etc. Payment application 175 may be further configured to determine the existence of and to manage accounts for user 105, as well as create new accounts if necessary.

Figure 2:
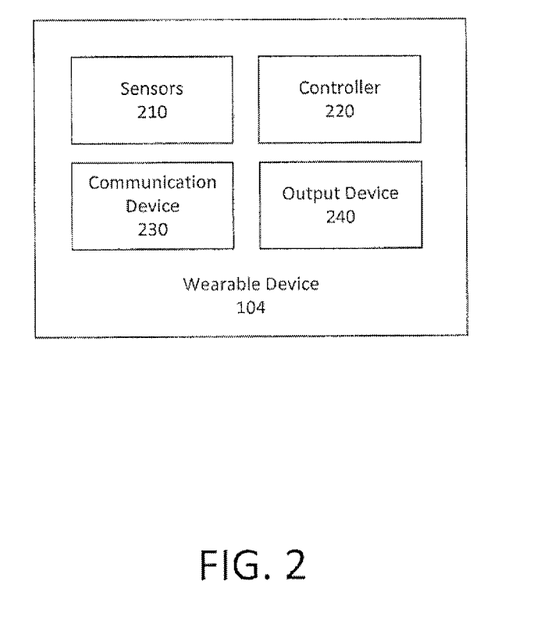
FIG. 2 is a block diagram of a wearable device suitable for implementing user authentication according to one embodiment.

FIG. 2 is a block diagram of a wearable device suitable for implementing user authentication according to one embodiment. Wearable device 104 may be a wearable item that may be worn by the user 105 or be attached to the user 105 or other items carried by the user 105. As such, the wearable device 104 may be a personal item to the user 105 that is worn or carried by the user 105. The wearable device 105 may include one or more of a sensor 210 configured to detect and/or monitor a body chemistry of the user 105, such as a smell, a scent, heart rate, blood chemistry, and the like.

In an embodiment, the sensor 210 may include an olfactory sensor. The olfactory sensor may be configured to detect smells or scents of the user 105 or smells or scents around the user 105. In particular, the olfactory sensor may include an electronic "nose" configured to detect smells, scents, or odors. The olfactory sensor may include an array of sensors that are reactive to certain chemical compounds. When the certain chemical compounds are absorbed by the sensors, a chemical reaction may occur that changes a physical or electrical property of the sensor. The change may be recorded by an electronic interface that transforms the response into an electrical signal. The generation of the electrical signals may indicate the detection of certain chemical compounds, such as certain smells, scents, or odors.

The olfactory sensor may be a metal-oxide-semiconductor (MOSFET) type sensor. The MOSFET type sensor may include a transistor configured to amplify or switch electronic signals. When chemical molecules or compounds are captured by a sensing portion, the chemical molecules or compounds may electrically charge (positively or negatively) the sensing portion or the electric field inside the MOSFET. Based on the electric signal pattern detected by the MOSFET, the system may analyze and determine a type, intensity, or concentration of the detected chemical compound or chemical molecule.

The olfactory sensor may be an organic polymer type sensor. The organic polymer may be configured to conduct electricity. The olfactory sensor may be a quartz crystal microbalance type sensor. The quartz crystal microbalance type sensor may be configured to measure mass per unit area by measuring the change in frequency of a quartz crystal resonator. In another embodiment, the olfactory sensor may be a micro-electro-mechanical device (MEMS) configured to implement surface acoustic wave to sense a physical phenomenon. In some embodiments, the sensors 210 may include one or more of the different types of olfactory sensors to provide a broad range of sensing ability.

The olfactory sensors may first be trained to recognize or distinguish certain smells, scents, or odors of the user 105 or perfumes/colognes worn by the user 105. In particular, the controller 220 or the user device 110 may learn the specific signal patterns generated by the olfactory sensors from detecting the smell or scent of the user 105 when the wearable device 104 is worn by the user 105. The specific signal pattern may be updated over time as the smells or scents of the user 105 or the perfumes or colognes worn by the user 105 (or interactions of perfumes or colognes with the user body chemistry) may change over time. In some embodiments, the controller 220 or the user device 110 may learn and store different scent profiles of the user 105 for different times of the day, days of the week or different seasons of the year. For example, the user 105 may wear a perfume on week days, but not on weekends. In another example, the user may typically work out at a certain time of the day. Thus, the user 105 may have a scent profile for week days and another scent profile for weekends. The user device 110 or the payment provider server 170 may select a body chemistry profile based on different environmental settings, locations, or settings. For example, based on the location detected, the user device 110 or the payment provider server 170 may select a body chemistry profile of the user 105 to compare with the body chemistry conditions detected at the wearable device 104 for user authentication.

The sensors 210 may include a blood chemistry sensor. In particular, the sensors 210 may include a blood glucose sensor configured to perform non-invasive detection of glucose level in the user 105's blood. The blood glucose sensor may be an optical type blood glucose sensor configured to measure blood glucose level by using near infrared detection techniques. In some embodiments, the blood glucose sensor may utilize ultrasound or dielectric spectroscopy to detect blood glucose level.

The blood chemistry sensor may include a blood-oxygen sensor. The blood-oxygen sensor may include a light emitting device that shines light onto the user 105 and light sensing devices that detect how much light is reflected back absorbed by the user 105 to detect how much oxygen is in the user 105's blood. Darker blood absorbs more light and has less oxygen level while lighter blood absorbs less light and has higher oxygen level.

The blood chemistry sensor may include a blood pressure sensor configured to measure a blood pressure of the user 105. The blood pressure sensor may measure an electrocardiogram (EKG) of the user 105 to measure the blood pressure of the user 105. In some embodiments, the blood pressure sensor may measure the user 105's pulse wave velocity between two points of user 105's body to measure the user 105's blood pressure.

The sensors 210 may include a heart rate sensor configured to detect a heart rate or a heart beat pattern of the user 105. The heart rate sensor may include a sensor configured to detect the electrical signals emitted from the user 105's heart when the heart beats. The controller 220 or the user device 110 may then determine the rate, the pattern, the frequency and other characteristics of the heart conditions of the user 105 based on the detection at the heart rate sensor.

The sensors 210 may include a skin conductance sensor configured to detect a skin conductance of the user 105. The skin conductance sensor may include a galvanic skin sensor configured to measure a galvanic skin response of the user 105. The galvanic skin sensor may detect a resistance between two points of the user 105's skin. The galvanic skin sensor also may detect a voltage difference between two points of the user 105's skin. The user 105's galvanic skin response may vary based on the user 105's mental state, physical state, and body response to ambient environments.

The sensors 210 may include a body temperature sensor configured to detect a body temperature of the user 105. In an embodiment, the body temperature sensor may include an ambient temperature sensor configured to detect an ambient temperature around the user 105. As such, the user's body temperature response to the ambient temperature may be detected.

In some embodiments, different types of sensors may be used in coordination with each other to provide better detection. For example, multiple types of body chemistry may be detected and the more types of body chemistry detected that match the body chemistry of the user, the higher probability that the wearable device 104 is worn by the user.

The wearable device 104 may include a communication device 230 configured to communicate with other devices. The communication device 230 may include a short range communication device, such as a Bluetooth or Bluetooth Low Energy (BLE) communication device, a Near-Field Communication (NFC) device, WiFi, or a combination thereof. In an embodiment, the communication device 230 may include a signal emitter configured to emit a wireless signal, without receiving communication from others. The communication device 230 may be configured to emit a unique wireless signal including unique patterns and/or frequencies, without a signal receiver. As such, the wearable device 104 may remain compact and low cost. In another embodiment, the communication device 230 may be configured to include a signal transmitter and a signal receiver to emit and receive communication signals. The signal range of the communication device 230 may be limited to a few feet, such that nearby devices may detect and/or communicate wirelessly.

The wearable device 104 may include a controller 220 configured to manage and control various operations of the wearable device 104. The controller 220 may include a microprocessor, an integrated circuit, or a combination thereof. The controller 220 may be configured or programmed to receive signals from the sensors 210 and make determinations or decisions regarding controlling the operations of other devices, such as a communication device 230 and/or the output device 240. For example, based on the signals received from the sensors, the controller 220 may determine whether the wearable device 104 is still worn by the user and may control the communication device 230 to emit signals accordingly. The controller 220 also may control the communication device 230 to communicate detection results to the user device 110.

The wearable device 104 may include an output device 240 configured to communicate with user 105. For example, output device 240 may be an audio signal emitter configured to emit audio signals to the user 105. In another example, output device 240 may be an LED component configured to provide visual output. In still another example, output device 240 may be a vibration device configured to vibrate to communicate with user 105. In some embodiments, output device 240 may include one or more types of different output devices, such as a combination of an LED component and an audio signal emitter to provide different types of outputs to the user 105.

The wearable device 104 may be powered by a battery, which may be a rechargeable battery. For example, the wearable device 104 may be powered by solar battery or by kinetic energy, such as the movement of user 105. In another example, the wearable device 104 may be powered by replaceable batteries.

Figures 3A, 3B:
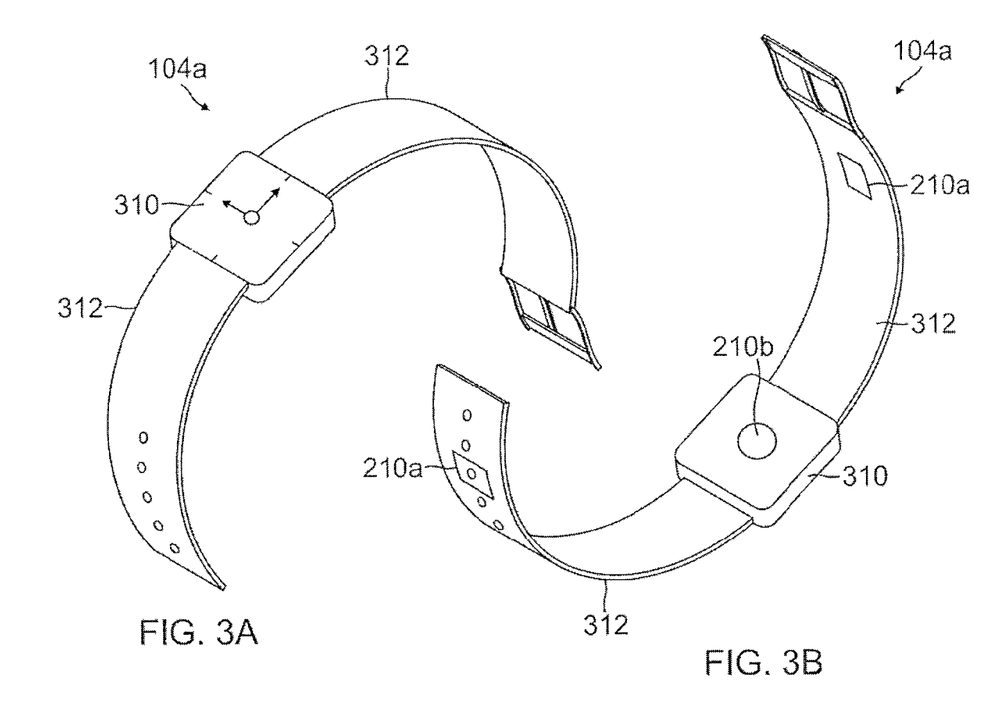
FIG. 3A is a diagram illustrating a perspective front view of a watch type wearable device according to one embodiment.
FIG. 3B is a diagram illustrating a perspective rear view of the watch type wearable device of FIG. 3A according to one embodiment.

FIG. 3A is a diagram illustrating a perspective front view of a watch type wearable device 104a according to one embodiment. The watch type wearable device 104a may include a watch case 310 within which various components, such as sensors 210, controller 220, communication device 230 and output device 240, are disposed. The watch case 310 may include a front surface configured to display time. The front surface may be a glass surface and may include a touch screen configured to receive inputs from the user 105. The watch type wearable device 104a also may include fastening portions 312 configured to fasten the watch type wearable device 104a to the user 105.

FIG. 3B is a diagram illustrating a perspective rear view of the watch type wearable device 104a of FIG. 3A according to one embodiment. The rear surface of the watch case 310 may include a sensor 210b. When the watch type wearable device 104a is worn by the user 105 or fastened to the user 105, the rear surface may contact the user 105, such as a wrist of the user 105. The sensor 210b provided on the rear surface also may contact the user 105. The sensor 210b may include one or more types of body chemistry sensors configured to detect the body chemistry of the user 105 when the watch type wearable device 104a is worn by the user 105 and the sensor 210b comes into contact with the user 105.

Figure 3C:
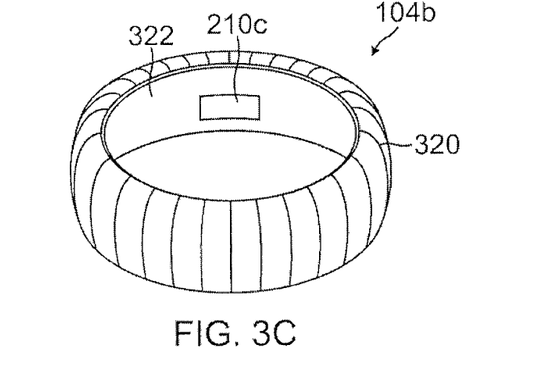
FIG. 3C is a diagram illustrating a perspective view of a band type wearable device according to one embodiment.

FIG. 3C is a diagram illustrating a perspective view of a band type wearable device 104b according to one embodiment. The band type wearable device 104b may include a band body 320 within which various components, such as sensors 210, controller 220, communication device 230 and output device 240, are disposed. The band body 320 may include an inner surface 322 configured to contact the user 105 when the band type wearable device 104b is worn by the user 105.

The inner surface 322 of the band body 320 may include a sensor 210c. When the band type wearable device 104b is worn by the user 105 or fastened to the user 105, the inner surface 322 may contact the user 105, such as a wrist of the user 105. The sensor 210c provided on the inner surface 322 also may contact the user 105. The sensor 210c may include one or more types of body chemistry sensors configured to detect and monitor various types of body chemistry of the user 105 when the band type wearable device 104b is worn by the user 105 and the sensor 210c comes into contact with the user 105. The band type wearable device 104b may be a functional wrist band or a jewelry piece, such as a wrist band, a neck collar, and the like.

Figure 3D:
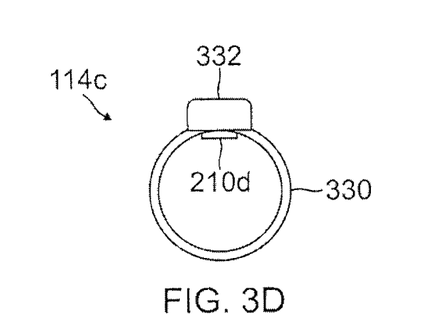
FIG. 3D is a diagram illustrating a perspective view of a ring type wearable device according to one embodiment.

FIG. 3D is a diagram illustrating a perspective view of a ring type wearable device 104c according to one embodiment. The ring type wearable device 104c may include a ring body 330 and a setting 332. Various components, such as sensors 210, controller 220, communication device 230 and output device 240, may be disposed in the ring body 330 and/or setting 332. A sensor 210d may be provided at the setting 332. When the ring type wearable device 104c is worn by the user 105, a bottom surface or inner surface of the ring body 33 and setting 332 may contact the user 105. The sensor 210d provided on the inner surface also may contact the user 105. The sensor 210d may include one or more types of body chemistry sensor be one or more of a pressure sensor, a contact sensor, a temperature sensor, an actuator type sensor, and the like that is configured to detect the user 105 when the ring type wearable device 104c is worn by the user 105 and the sensor 210d comes into contact with the user 105.

Figure 3E:
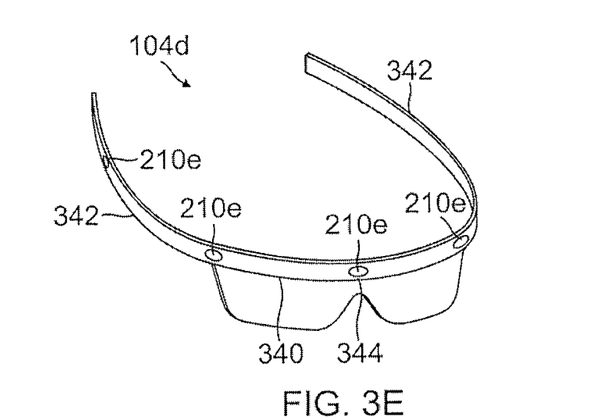
FIG. 3E is a diagram illustrating perspective view of a glasses type wearable device according to one embodiment.

FIG. 3E is a diagram illustrating perspective view of a glasses type wearable device 104d according to one embodiment. The glasses type wearable device 104d may include an eyeglass frame including temple portions 342 connected to lens frames 340 via hinges 346. The lens frames 340 include a bridge portion 344. Various components, such as sensors 210, controller 220, communication device 230 and output device 240, may be disposed in the glass frame. In an example, sensors 210e may be provided on the bridge portion 344 to detect user contacts. Sensors 210e also may be provided on inner surfaces of temple portions 342 to detect user contacts. The sensor 210e may include one or more types of body chemistry sensors that are configured to detect various types of body chemistry of the user 105.

Figure 3F:
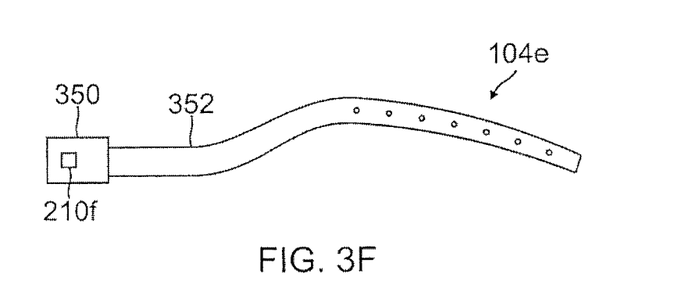
FIG. 3F is a diagram illustrating perspective view of a belt type wearable device according to one embodiment.

FIG. 3F is a diagram illustrating perspective view of a belt type wearable device 104e according to one embodiment. The belt type wearable device 104e may include a belt buckle portion 350 and a belt portion 352. Various components, such as sensors 210, controller 220, communication device 230 and output device 240, may be disposed in belt buckle portion 350. In an example, a sensor 210f may be provided at the belt buckle portion 350. The sensor 210f may include one or more types of body chemistry sensors configured to detect various types of body chemistry of the user 105.

Other types of wearable devices 104 that may be attached to or carried by the user 105 also may be utilized. For example, the wearable device 104 may be earrings, ear buds, or a clip configured to attach to the user 105 or items carried by the user 105. In another example, the wearable device 104 may be a tab that may be inserted or placed inside a bag or a wallet of the user 105.

Figure 5:
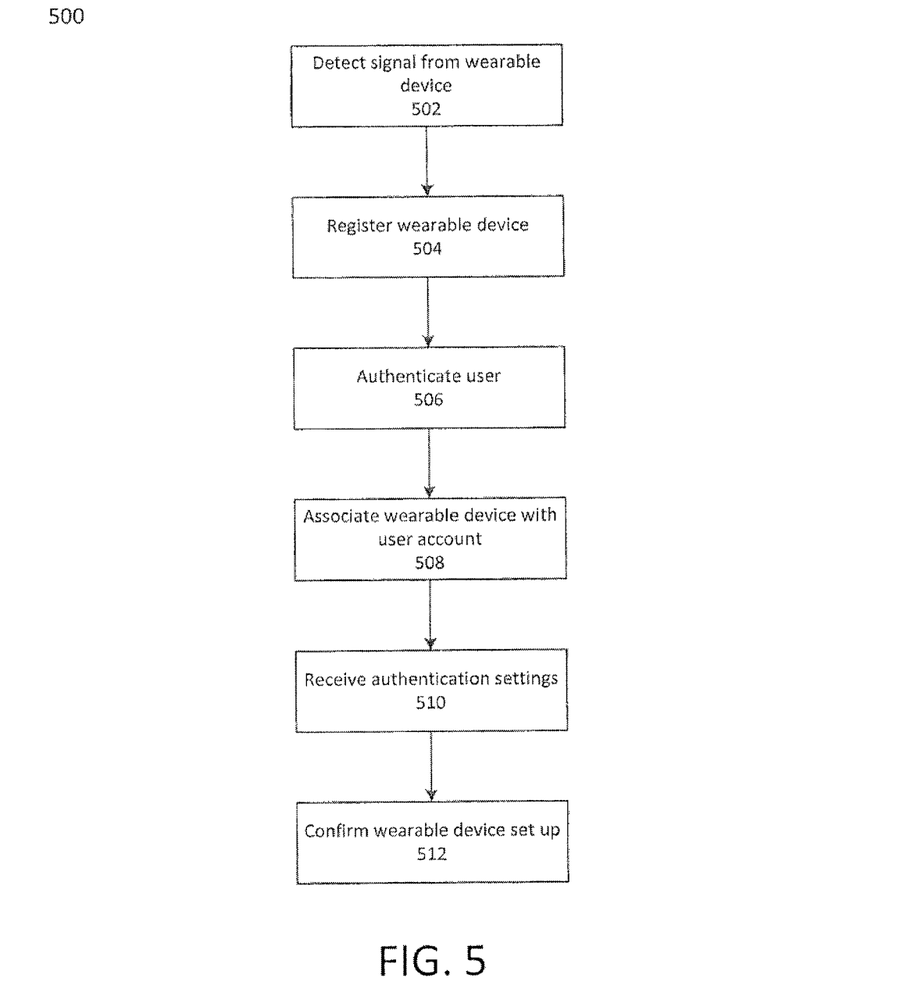
FIG. 5 is a flow chart illustrating a set up process for implementing user authentication via a wearable device according to one embodiment.

FIG. 5 is a flow chart illustrating a set up process 500 for implementing user authentication via a wearable device according to one embodiment. Initially, the 105 may put the wearable device 104 on and may turn on, if needed, the wearable device 104. The user may also be required to enter authentication information, such as a password or PIN, so that the system can associate the user (and corresponding account(s)) with body chemistry data. The wearable device 104 may then detect, by one or more sensors 210, that the wearable device 104 is being worn by the user 105. The controller 220 of the wearable device 104 may encode the detected body chemistry conditions into a signal and control the communication device 230 to send the signal including information regarding the user 105's body chemistry conditions to the user device 110. The wireless signals may be emitted at a particular frequency or pattern associated with the wearable device 104. For example, different types of wearable devices may have different frequencies or patterns. In another example, the signal may be encrypted and may include information representing a unique device ID of the wearable device 104. The signal may include the detected body chemistry conditions of the user 105, such as body temperature, heart beats, smells, scents, and the like. The signal may be emitted periodically, such as every 5 seconds or every 10 seconds, as long as the wearable device 104 is worn by the user 105. The signal also may carry information related to the wearable device 104, such as type, name, ID, description, specification, and/or status (whether worn by the user) of the wearable device 104.

At step 502, the user device 110 may detect the signal emitted from the wearable device 104. For example, the user device 110 may be carried by the user 105 or the user 105 is currently using the user device 110. As such, the user device 110 may be located within the wireless broadcast range of the wearable device 104. At step 504, the user device 110 may register or receive the signal. The user device 110 may analyze the signal from the wearable device 104 and may determine that the signal is from a wearable device for user authentication. The user device 110 may ask the user 105 whether the user 105 would like to register the wireless signal for user authentication. If so, the user 105 may be allowed to designate one or more user accounts which may use the signal for user authentication. For example, the user may associate the wireless signal with user 105's payment account at a payment service provider. As such, the wireless signal may be used to authenticate user for that payment account.

In an embodiment, the user device 110 or the payment provider server 170 may set up various body chemistry profiles for the user 105. In particular, based on the types of sensors available on the wearable device 104, body chemistry profiles may be set up for detected conditions by the sensors at the wearable device 104. For example, the wearable device 104 may include a body temperature sensor, a heart beat sensor, an ambient temperature sensor, and an olfactory sensor. The system may set up a body chemistry profile for storing these measurements of the user 105. For example, a body chemistry profile may include the user 105's body temperature, heart beat, and smell or scent that are specific to the user 105. In an embodiment, different body chemistry profiles may be set up for the user 105 for different environments or situations as the user 105 may have different body chemistry measurements for different environments or situations, including at different times of the day, different days of the week, different months/seasons of the year, and/or different locations (e.g., a vacation location, a work location, a home location, a specific store location, etc.). For example, the user 105 may have a body chemistry profile for when the user 105 is exercising, a body chemistry profile for when the user 105 is working in the office, a body chemistry profile for when the user 105 is shopping, and the like. The system may learn the user 105's body chemistry by monitoring the user 105's various body chemistry conditions in different settings and environments. The system may analyze and determine patterns or signatures of body chemistry conditions specific to the user 105. These specific patterns or signatures may be used to distinguish the user 105 from others and may be used to authenticate the user 105. For example, the user 105 may have a specific heart beat pattern, a specific heart beat response to change in ambient temperature, a specific body temperature response to change in ambient temperature, and the like.

In some embodiments, the system also may analyze different types of body chemistry conditions and other environmental factors, such as temperature, humidity, atmosphere pressure, weather, and the like. The system may determine correlations between different type types of body chemistry conditions and environmental factors. These correlations may be specific to the user 105. For example, the user 105 may have a specific change or rate of change in body temperature in response to change in ambient temperature. In another example, the user 105 may have a specific change or rate of change in galvanic skin response in response to change in body temperature or change in heart rate.

At step 506, the user device 110 may authenticate user 105 for the designated account. For example, the user device 110 may ask for the user's login ID, password, finger-print scan, and the like. When the user 105 is authenticated successfully, the user device 110 may then associate the body chemistry conditions measured at the wearable device 104 with the user 105 or with the user's designated accounts at step 508. As such, the body chemistry conditions measured at the wearable device 104 may be associated with the user 105 or with the user 105's account and may later be used to authenticate the user 105 automatically.

At step 510, the user device 110 may allow the user 105 to select or input authentication settings for the designated accounts with regard to the signals. In particular, the user 105 may customize the authentication process for the designated accounts with regard to how the user 105 should be authenticated for different user accounts. For example, the user 105 may designate accounts that require lower security requirement, such as email accounts, social media account, and the like. The system may have less security requirement for user authentication to access these accounts. As such, the system may require less body chemistry measurements to authenticate the user. For example, the system may measure the current body chemistry conditions and determine how many types of body chemistry conditions match those in the user 105's profile. The system may require at least two out of five types of currently measured body chemistry conditions to match the body chemistry conditions of the user 105's profile to automatically authenticate the user 105 into these accounts. The system may require more matches (four or five out of five types of body chemistry) for accounts that require higher security requirements, such as financial accounts, bank accounts, payment accounts, and the like.

In an embodiment, different types of body chemistry may be weighted different for the purpose of user authentication. In particular, the types of body chemistry that are more unique or specific to the user 105 may be weighted more than other types of body chemistry that are not as unique or specific to the user 105. For example, the user 105's heart beat patterns or EKG may be weighted more than the user 105's heart rate for the purpose of user authentication, cause the user 105's heart beat pattern or EKG is more unique to the user 105 than the heart rate of the user 105, which is simply a number. In another example, the user 105's body temperature response to changes in ambient temperature may be weighted more than the user 105's static body temperature, because the user 105's body response to change in ambient temperature is more unique than a static measurement of the user 105's body temperature. Therefore, the types of body chemistry that are more unique or specific to the user 105 may be weighted more to provide better assessment for user authentication.

In an embodiment, the system may allow the user 105 to set how long the user 105 should be kept logged in at an account. For example, if the user device 110 determines that the user 105 is wearing the wearable device 104 based on the signals received from the wearable device 104, the user device 110 may keep the user 105 logged in as long as the user device 110 determines that the user 105 is still wearing the wearable device 104. The user device 110 may log user 105 out after a predetermined amount of time (which can be immediately) if the user device 110 detettnines that the user 105 no longer is wearing the wearable device 104. In other embodiments, the system sets this time period, such as based on various security factors.

In an embodiment, if the user device 110 detects the signals from the wearable device 104 indicating that the user 105 is wearing the wearable device 104, the user device 110 may automatically authenticate the user 105 or log the user 105 into the designated account without requiring credentials, such as passwords or login IDs. In still another embodiment, if the user device 110 detects the signals from the wearable device 104 indicating that the user 105 is wearing the wearable device 104, the user device 110 may require less credentials for authentication or have less strict security requirements. The user 105 may select and customize how the wearable device 104 may provide different features of user authentication for different user accounts.

In an embodiment, the user device 110 may allow the user to designate a combination of different signals from different wearable devices for a particular account. For example, different wearable devices may be worn by the user 105 to detect different types of body chemistry conditions. Automatic user authentication may be implemented for a particular account when the user device 110 detects that the user 105 is wearing both a particular ring type wearable device and a particular watch type wearable device. In an embodiment, different combinations of wearable devices may be designated for different authentication requirements. For example, when the user 105 is wearing a particular combination of three wearable devices, the authentication requirement may be less than when the user 105 is wearing two of the three wearable devices.

In an embodiment, one wearable device 104 may be used to provide authentication for multiple of user's accounts. For example, when the user 105 is wearing a particular watch type wearable device 104a, the user device 110 may keep the user 105 logged in at the user 105's bank account and at the user 105's shopping account. In another embodiment, different types of body chemistry measurements may provide different levels of authentication requirement. For example, measurements from a wearable device with heart beat monitors may allow automatic access to an account, while measurements from another wearable device with a body temperature sensor may still require the user 105 to enter his/her user ID.

At step 512, the user device 110 may confirm set up with the user 105. For example, a notification may be provided on the user device 110 to inform the user 105 that a particular wearable device 104 is now set up for user authentication of a particular user's account. In another example, the output device 240 at the wearable device 104 may confirm the set up by beeping, LED flashing or color change, vibrations, or information display (on a screen). The user device 110 may store and update the authentication settings of various accounts of the user 105 and their respective associated wearable devices. The user device 110 may provide a user interface for the user 105 to update, add, delete, and/or modify the authentication settings related to wearable devices.

Figure 6:
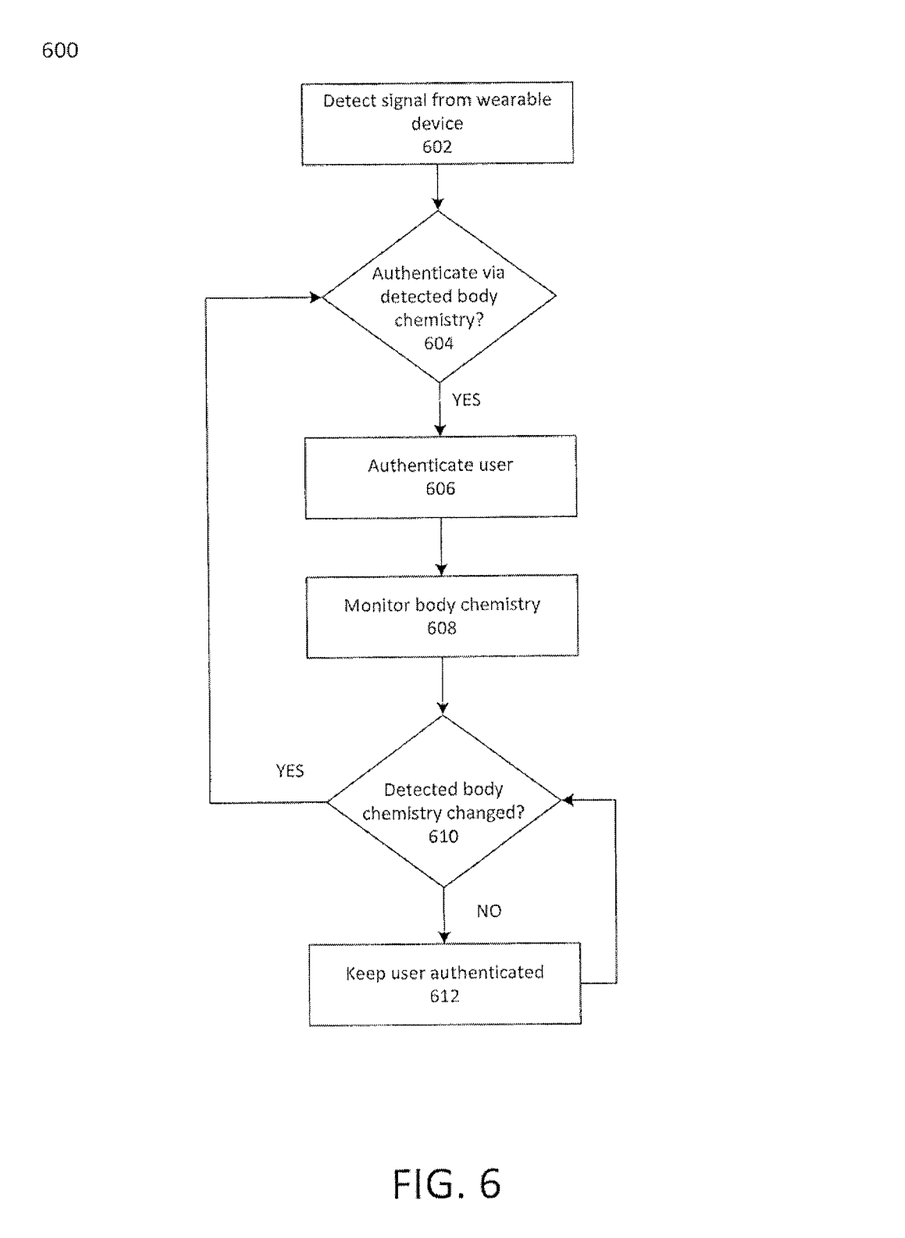
FIG. 6 is a flow chart illustrating a method for implementing user authentication via a wearable device according to one embodiment.

FIG. 6 is a flow chart illustrating a method 600 for implementing user authentication via a wearable device configured to detect body chemistry according to one embodiment. At step 602, the user device 110 may detect signals from a wearable device 104. For example, when the user 105 puts on the wearable device 104, the wearable device 104 may detect the user 105 via sensors 210 and may begin to emit signals indicating the user 105's body chemistry conditions. In an embodiment, the wearable device 104 may previously have been registered with the user device 110, such that the wearable device 104 may automatically be paired with the user device 110, e.g., via Bluetooth communication.

At step 604, the user device 110 may determine whether the signals contain information regarding body chemistry conditions of the user 105 for user authentication. In particular, the user device 110 may check and see if the received signals are associated with one or more of the user 105's registered wearable devices. If so, the user device 110 also may look up the authentication settings to determine the user 105's body chemistry profile which defines the user 105's unique body chemistry conditions. The system also may check to see how the measured body chemistry conditions may alter the authentication process for the account.

In an embodiment, the system may calculate a similarity score indicating how similar the body chemistry conditions measured at the wearable device 104 are to the body chemistry conditions of the user 105 defined in the user 105's body chemistry profile. The similarity score may be calculated based on how many types of body chemistry are measured, how many of them are closely matched to the ones in the user 105's profile, how closely each body chemistry condition is matched, and the like. Based on the similarity score and the security requirement of a particular user account, the system may determine how the user 105 should be authenticated. For example, the user 105's bank account may have higher security requirement and may require a higher similarity score threshold to automatically log in the user 105. The user 105's social networking account may have a lower security requirement and may require a lower similarity score threshold to automatically log in the user 105. In an embodiment, different similarity score may result in different user authentication requirements. For example, a higher similarity score may result in the system requiring the user name to log in while a lower similarity score may require both the user name and the password to log in. The system may also base authentication on other data in conjunction with the body chemistry data, such as, but not limited to, a user location, a time of day, a day of the year, and transaction details (amount of transaction, merchant information, item description(s), etc.

At step 606, the user device 110 may authenticate the user 105 based on the authentication settings for the designated account in view of the measured body chemistry conditions. For example, if the user 105 has not been logged into the account, the user device 110 may log the user 105 in automatically without requiring user credentials when the measured body chemistry conditions very closely match that of the user's body chemistry defined in the user's profile. If the user 105 already is logged into the account, the user device 110 may maintain the logged in session in view of the signals received from the wearable device 104.

At step 608, the user device 110 or the wearable device 104 may continue to measure and monitor the body chemistry conditions of the user 105 or the wearer at the wearable device 104. For example, the wearable device 104 may measure the body chemistry and communicate the results periodically, e.g., every few seconds. The user device 110 may determine whether the signals are received periodically from the wearable device 104 and whether the body chemistry conditions measured at the wearable device 104 still match those defined in the user 105's profile at step 610.

If the user device 110 continues to receive the signals from the wearable device 104 and the body chemistry conditions measured at the wearable device 104 still match the user 105's body chemistry conditions defined in user profile, the user device 110 may keep the user 105 authenticated at step 612. For example, the user device 110 may keep the user 105 logged in at the account. In another example, the user device 110 may continue to allow a lower security requirement or authentication requirement for logging in. The process then may go back to step 610 where the user device 110 continues to check whether the signals from the wearable device 104 still are detected at the user device 110.

If the user device 110 stops receiving the signals from the wearable device 104 or the measured body chemistry conditions at the wearable device 103 are changed, which indicates that the wearable device is taken off from the user 105 or someone else is wearing the wearable device 104, the user device 110 may log user 105 out of the account or stop authenticating the user 105 immediately or within a certain time period, which may depend on user, system, and/or account settings. In another example, the user device 110 may require higher or stricter authentication requirements when the user 105 is not wearing the wearable device 104.

After the wearable device 104 has been taken off from the user 105, the user device 110 may require that the user 105 provide authentication credentials to log in again even if the wearable device 104 has been put back on the user 105. This may ensure that the wearable device 104 is not worn by another user for the purpose of unauthorized access to the user's account.

By implementing processes 500 and 600, a wearable device 104 may be provided to facilitate easier and safer authentication process for the user 105. In particular, the wearable device 104 may include sensors that may detect and/or monitor the user 105's body chemistry conditions. The wearable device 104 may be configured to emit signals indicating body chemistry conditions measured at the wearable device 104. Based on how the measured body chemistry conditions are matched to the body chemistry conditions of the user 105 defined in the user 105's body chemistry profiles, the user device 110 may allow automatic or easier authentication process for the user's account. The automatic or easier authentication may end once the measured body chemistry conditions no longer match those of the user 105's profiles or when the wearable device 104 is taken off from the user 105.

In the above embodiments, the wearable device 104 is utilized for authentication into user's accounts at the user device 104. In another embodiment, the wearable device 104 may be utilized for user authentication for access into buildings, areas, events, vehicles, transportation networks, and any location where user authentication is required.

Figure 4:
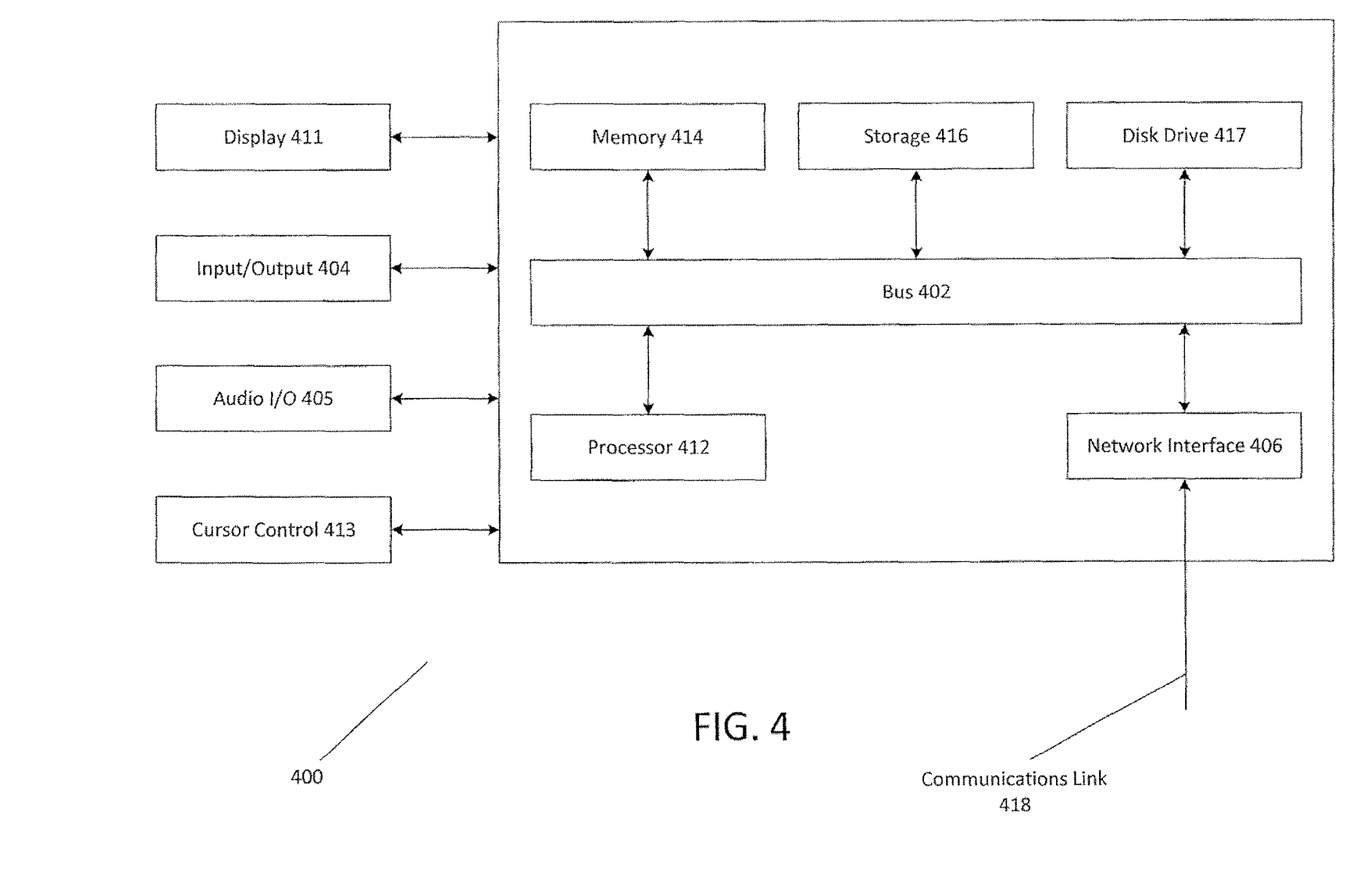
FIG. 4 is a block diagram of a computer system suitable for implementing one or more components in FIG. 1 according to one embodiment.

FIG. 4 is a block diagram of a computer system 400 suitable for implementing one or more embodiments of the present disclosure. In various implementations, the user device may comprise a personal computing device (e.g., smart phone, a computing tablet, a personal computer, laptop, Bluetooth device, key FOB, badge, wearable computing device, etc.) capable of communicating with the network. The merchant and/or payment provider may utilize a network computing device (e.g., a network server) capable of communicating with the network. It should be appreciated that each of the devices utilized by users, merchants, and payment providers may be implemented as computer system 400 in a manner as follows.

Computer system 400 includes a bus 402 or other communication mechanism for communicating information data, signals, and information between various components of computer system 400. Components include an input/output (I/O) component 404 that processes a user action, such as selecting keys from a keypad/keyboard, selecting one or more buttons or links, etc., and sends a corresponding signal to bus 402. I/O component 404 may also include an output component, such as a display 411 and a cursor control 413 (such as a keyboard, keypad, mouse, etc.). An optional audio input/output component 405 may also be included to allow a user to use voice for inputting information by converting audio signals. Audio I/O component 405 may allow the user to hear audio. A transceiver or network interface 406 transmits and receives signals between computer system 400 and other devices, such as another user device, a merchant server, or a payment provider server via network 160. In one embodiment, the transmission is wireless, although other transmission mediums and methods may also be suitable. A processor 412, which can be a micro-controller, digital signal processor (DSP), or other processing component, processes these various signals, such as for display on computer system 400 or transmission to other devices via a communication link 418. Processor 412 may also control transmission of information, such as cookies or IP addresses, to other devices.

Components of computer system 400 also include a system memory component 414 (e.g., RAM), a static storage component 416 (e.g., ROM), and/or a disk drive 417. Computer system 400 performs specific operations by processor 412 and other components by executing one or more sequences of instructions contained in system memory component 414. Logic may be encoded in a computer readable medium, which may refer to any medium that participates in providing instructions to processor 412 for execution. Such a medium may take many forms, including but not limited to, non-volatile media, volatile media, and transmission media. In various implementations, non-volatile media includes optical or magnetic disks, volatile media includes dynamic memory, such as system memory component 414, and transmission media includes coaxial cables, copper wire, and fiber optics, including wires that comprise bus 402. In one embodiment, the logic is encoded in non-transitory computer readable medium. In one example, transmission media may take the form of acoustic or light waves, such as those generated during radio wave, optical, and infrared data communications.

Some common forms of computer readable media includes, for example, floppy disk, flexible disk, hard disk, magnetic tape, any other magnetic medium, CD-ROM, any other optical medium, punch cards, paper tape, any other physical medium with patterns of holes, RAM, PROM, EEPROM, FLASH-EEPROM, any other memory chip or cartridge, or any other medium from which a computer is adapted to read.

In various embodiments of the present disclosure, execution of instruction sequences to practice the present disclosure may be performed by computer system 400. In various other embodiments of the present disclosure, a plurality of computer systems 400 coupled by communication link 418 to the network (e.g., such as a LAN, WLAN, PTSN, and/or various other wired or wireless networks, including telecommunications, mobile, and cellular phone networks) may perform instruction sequences to practice the present disclosure in coordination with one another.

Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

Software, in accordance with the present disclosure, such as program code and/or data, may be stored on one or more computer readable mediums. It is also contemplated that software identified herein may be implemented using one or more general purpose or specific purpose computers and/or computer systems, networked and/or otherwise. Where applicable, the ordering of various steps described herein may be changed, combined into composite steps, and/or separated into sub-steps to provide features described herein.

The foregoing disclosure is not intended to limit the present disclosure to the precise forms or particular fields of use disclosed. As such, it is contemplated that various alternate embodiments and/or modifications to the present disclosure, whether explicitly described or implied herein, are possible in light of the disclosure. Having thus described embodiments of the present disclosure, persons of ordinary skill in the art will recognize that changes may be made in form and detail without departing from the scope of the present disclosure. Thus, the present disclosure is limited only by the claims.

What is claimed is:

1. A system comprising:
   a non-transitory memory; and
   one or more hardware processors coupled to the non-transitory memory and configured to read machine-executable instructions to cause the system to perform operations comprising:
   receiving, via a communication with a first device, first body chemistry conditions of a user of the first device;
   accessing user body chemistry conditions from a body chemistry profile associated with an account of the user;
   calculating a first similarity score indicating a degree of similarity between the first body chemistry conditions and the user body chemistry conditions;
   authenticating the user to a first account with a first authentication criteria based on the first similarity score;
   receiving second body chemistry conditions of the user;
   in response to receiving the second body chemistry conditions, calculating a second similarity score between the second body chemistry conditions and the user body chemistry conditions; and
   authenticating the user to a second account with a second authentication criteria based on a combination of the first similarity score and the second similarity score, wherein the second account has a higher security requirement than the first account.

2. The system of claim 1, wherein the operations further comprise:
   determining the second authentication criteria in response to a type of the first body chemistry condition and a type of the second body chemistry condition.

3. The system of claim 1, wherein the operations further comprise:
   requesting additional information if the first similarity score is below a similarity score threshold to authenticate the user to the first account.

4. The system of claim 1, wherein a value of the first authentication criteria is less than a value of the second authentication criteria.

5. The system of claim 1, wherein the second body chemistry conditions is received from a second device and the operations further comprise:
   determining a first device type of the first device and a second device type of the second device; and
   determining second authentication criteria based on the first device type and the second device type.

6. The system of claim 1, wherein the operations further comprise:
   determining that the second body chemistry conditions are no longer being received; and
   ceasing authentication of the user to the second account in response to no longer receiving the second body chemistry conditions.

7. The system of claim 1, wherein the account of the user comprises different body chemistry profiles for different environmental settings.

8. The system of claim 7, wherein the operations further comprise:
   selecting the body chemistry profile from a plurality of body chemistry profiles for the user based on the first body chemistry conditions detected.

9. The system of claim 1, wherein the first similarity score and the second similarity score are each determined based on a respective number of body chemistry conditions matching those of the body chemistry profile of the user.

10. The system of claim 2, wherein a first type of body chemistry has a greater weighted value in determining the similarity score compared to a second type of body chemistry.

11. A method for authenticating accounts using body chemistry, the method comprising:
    receiving first body chemistry conditions of a user of a first device from the first device;
    calculating a first similarity score indicating a degree of similarity between the first body chemistry conditions and user body chemistry conditions stored in a body chemistry profile in an account of the user;

authenticating the user to a first account with a first authentication criteria based on the first similarity score;

receiving a second body chemistry conditions of the user;

in response to receiving the second body chemistry conditions, calculating a second similarity score between the second body chemistry conditions and the user body chemistry conditions; and authenticating the user to a second account with a second authentication criteria based on a combination of the first similarity score and the second similarity score, wherein the second account has a higher security requirement than the first account.

12. The method of claim 11, further comprising:

determining the second authentication criteria in response to a type of the first body chemistry condition and a type of the second body chemistry condition.

13. The method of claim 11, further comprising:

requesting additional information if the first similarity score is below a similarity score threshold to authenticate the user to the first account.

14. The method of claim 11, wherein a value of the first authentication criteria is less than a value of the second authentication criteria.

15. The method of claim 11, wherein the second body chemistry conditions is received from a second device and further comprising:

determining a first device type of the first device and a second device type of the second device; and determining second authentication criteria based on the first device type and the second device type.

16. The method of claim 11, further comprising:

determining that the second body chemistry conditions are no longer being received; and ceasing authentication of the user to the second account in response to no longer receiving the second body chemistry conditions.

17. The method of claim 11, wherein the account of the user comprises different body chemistry profiles for different environmental settings.

18. The method of claim 17, further comprising:

selecting the body chemistry profile from a plurality of body chemistry profiles for the user based on the first body chemistry conditions detected at the first device.

19. The method of claim 11, wherein the first similarity score and the second similarity score are each determined based on a respective number of body chemistry conditions matching those of the body chemistry profile of the user.

20. A non-transitory machine-readable medium having stored thereon instructions executable to cause a machine to perform operations comprising:

receiving first body chemistry conditions of a user of a first device from the first device;

calculating a first similarity score indicating a degree of similarity between the first body chemistry conditions and user body chemistry conditions stored in a body chemistry profile in an account of the user;

authenticating the user to a first account with a first authentication criteria based on the first similarity score;

receiving second body chemistry conditions of the user;

in response to receiving the second body chemistry conditions, calculating a second similarity score between the second body chemistry conditions received and the user body chemistry conditions; and authenticating the user to a second account with a second authentication criteria based on a combination of the first similarity score and the second similarity score, wherein the second account has a higher security requirement than the first account.

* * * * *

UNITED STATES PATENT AND TRADEMARK OFFICE
CERTIFICATE OF CORRECTION

PATENT NO. : 10,135,819 B2
APPLICATION NO. : 15/389893
DATED : November 20, 2018
INVENTOR(S) : Tijerina et al.

Page 1 of 1

It is certified that error appears in the above-identified patent and that said Letters Patent is hereby corrected as shown below:

In the Specification

In the Detailed Description:

In Column 4, Line 65-66, change "infoitiiation" to --information--.

In Column 13, Line 23, change "detettnines" to --determines--.

Signed and Sealed this
Twenty-sixth Day of February, 2019

Andrei Iancu
*Director of the United States Patent and Trademark Office*